United States Patent
McShane

(10) Patent No.: US 7,078,023 B1
(45) Date of Patent: Jul. 18, 2006

(54) FOOT AND SHOE DEODORANT

(75) Inventor: James E. McShane, Memphis, TN (US)

(73) Assignee: Schering-Plough Healthcare Products Inc., Memphis, TN (US)

( * ) Notice: Subject to any disclaimer, the term of this patent is extended or adjusted under 35 U.S.C. 154(b) by 478 days.

(21) Appl. No.: 09/675,938

(22) Filed: Sep. 29, 2000

Related U.S. Application Data

(63) Continuation of application No. 09/216,578, filed on Dec. 18, 1998, now abandoned.

(60) Provisional application No. 60/068,643, filed on Dec. 23, 1997.

(51) Int. Cl.
*A61K 33/30* (2006.01)
*A61K 8/27* (2006.01)

(52) U.S. Cl. .................. 424/67; 424/45; 424/76.2; 424/76.4; 424/76.5; 424/641; 424/642

(58) Field of Classification Search .................. 424/67, 424/45, 76.2, 76.4, 76.5, 641, 642
See application file for complete search history.

(56) References Cited

U.S. PATENT DOCUMENTS

| | | | |
|---|---|---|---|
| 4,784,846 A | 11/1988 | Whaley | |
| 5,122,418 A | 6/1992 | Nakane et al. | |
| 5,223,244 A | 6/1993 | Moro et al. | |
| 5,466,470 A * | 11/1995 | Lajoie | 424/641 |
| 5,575,988 A | 11/1996 | Knowles, Jr. et al. | |
| 5,679,324 A | 10/1997 | Lisboa et al. | |

FOREIGN PATENT DOCUMENTS

| | | |
|---|---|---|
| WO | WO 95/02394 | 1/1995 |
| WO | WO 97/05855 | 2/1997 |

OTHER PUBLICATIONS

The Condensed Chemical Dictionary, 10$^{TH}$ Edition, Gessner G. Hawley, Van Nostrand Reinhold Co., New York, 1981, p. 23.
Webster's Ninth New Collegiate Dictionary, Merriam-Webster, Inc., 1988, p. 60.
NanoGard® Zinc Oxide (ZnO), Publication of Nanophase Technologies Corporation, Burr Ridge, Illinois, Sep. 20, 1996, 3 pages.
NanoGard® Zinc Oxide Material Safety Data Sheet, Publication of Nanophase Technologies Corporation, Burr Ridge, Illinois, Aug. 19, 1996, 4 pages.
MPEP Revision 3, 6$^{th}$ Edition, 1997.

* cited by examiner

*Primary Examiner*—Sreenivasan Padmanabhan
*Assistant Examiner*—Shahnam Sharareh
(74) *Attorney, Agent, or Firm*—Robert J. Lipka; Matthew J. Golden

(57) ABSTRACT

A pressurized aerosol and concentrate are described for treating moderate to severe foot and/or shoe odors. The aerosol contains micronized zinc oxide, a propellant and a solvent. Optionally, the aerosol may also contain a fragrance, a thickening agent and/or a base.

11 Claims, No Drawings

FOOT AND SHOE DEODORANT

This is a continuation of U.S. application Ser. No. 09/216,578 filed Dec. 18, 1998 now abandoned, which is based on Provisional Application No. 60/068,643, filed Dec. 23, 1997.

BACKGROUND

According to Robert T. Maleeny and William F. Palmer, Environmental Odor Control, Soap/Cosmetics/Chemical Specialties for January 1991, pp. 28–31, malodors are usually caused by chemicals that are perceived at very low concentrations. Although malodors may not be dangerous to health at low levels, they can affect one's enjoyment of the environment. Maleeny and Palmer disclose that the perfumers of ancient Egypt and Medieval Europe practised masking by deodorizing through the use of perfumes, colognes and sachets. Presently, mild to moderate foot odor is commercially treated with an array of currently marketed products. However, a need exists for a deodorant product which is also effective in the treatment of moderate to severe foot odor. It would also be desirable to provide a deodorant for treating a spectrum of foot and shoe odors, including moderate to severe foot odor.

SUMMARY OF THE INVENTION

The present invention is directed toward a pressurized aerosol for treating foot and/or shoe odors comprising:

a) micronized zinc oxide;

b) a propellant for expelling the contents of the aerosol when the pressure is released; and c) a solvent.

Optionally and preferably, the aerosol further comprises d) a fragrance to help mask any foot odors and/or provide a more pleasant odor to the foot or shoe. Also optional, the aerosol further comprises e) a thickening agent capable of thickening the mixture of the micronized zinc oxide, the propellant and the carrier or organic solvent. Also optionally, the aerosol further comprises g) a base to neutralize any organic or inorganic acids.

The present invention is also directed towards a composition or concentrate useful for treating foot and/or shoe odors comprising i) micronized zinc oxide;

ii) at least one solvent;

iii) at least one fragrance. Optionally, the concentrate may further comprise iv) at least one thickening agent. Also optionally, the concentrate may further comprise v) a base to neutralize any organic or inorganic acids.

The present invention is also directed towards a method for treating foot or shoe odors by applying to said foot or shoe a concentrate comprising:

i) micronized zinc oxide;

ii) at least one solvent;

iii) at least one fragrance.

The concentrate employed in the present method, optionally, may further comprise iv) at least one thickening agent. Also optionally, the concentrate employed in the present method may further comprise v) a base to neutralize any organic or inorganic acids. Preferably, the concentrate is contained within an pressurized aerosol and admixed with a propellant for expelling the contents of the aerosol when the pressure is released.

The present invention has the advantage of providing an aerosol and concentrate which are highly effective for treating foot and/or shoe odors.

Another advantage of the present invention is that it provides an aerosol and concentrate for treating foot and/or shoe odors that is easy to apply.

Another advantage of the present invention is that it provides an aerosol, a concentrate and a method for treating foot and/or shoe odors that effectively treats or reduces foot odors faster and more rapidly than other known methods or compositions.

Another advantage of the present invention is that it provides an aerosol and concentrate for treating foot and/or shoe odors that may have a reduced tendency to clog the nozzle or dispenser of the aerosol compared with other known compositions.

And still yet another advantage of the present invention is that it provides an aerosol and concentrate for treating foot and shoe odors that effectively eliminates or controls foot wetness faster or more rapidly than other known compositions.

DETAILED DESCRIPTION OF THE INVENTION

As used in the present specification, the terms "controlling" and "reducing," with regard to treating foot odor, are used interchangeably. Except as noted, the percentage of ingredients in the composition employed in the aerosol (including propellant) is by weight percent. However, the percentage of ingredients in the composition without the propellant (i.e. the concentrate) can be determined by recalculating the percentages of the ingredients.

Microcronized zinc oxide is employed in amounts effective for treating foot and/or shoe odors. Such amounts in the aerosol can range from about 0.5 to about 15% by weight in the composition of the aerosol, preferably from about 2 to about 12% by weight, more preferably from about 3 to about 10% by weight. Without or absent the propellant, the amount of micronized zinc in the concentrate can range from about one to about 90% by weight, preferably from about 10 to about 50% by weight, more preferably from about 15 to about 45% by weight. Physically, micronized zinc oxide is a white, odorless powder comprised of loosely aggregated ultra fine nanometer particles. The average particle size of the micronized zinc oxide can range from about 26 to about 46 nanometers (nm), preferably from about 30 to about 40 nanometers, more preferably about 35 to about 37 nm, most preferably about 36 nm. The specific surface area can range from about 20 to about 40 meters squared per gram ($m^2/g$), preferably from about 25 to about 35 $m^2/g$, more preferably about 30 $m^2/g$, using a test method of gas absorption, such as, for example, the Breunerhauer, Emmett, Edward and Teller (BEET) theory for measurement of surface area based upon absorption of gases to surfaces. The micronized zinc oxide should be applied to the foot and/or shoe in an amount effective to reduce foot and/or shoe odors. Such amounts can range from about 5 to about 250 milligrams of micronized zinc oxide per foot or shoe, preferably from about 50 to about 150 milligrams of micronized zinc oxide. Micronized zinc oxide is commercially available as for example from Nanophase Technologies Corporation, Burr Ridge, Ill. Alternatively, micron-sized particles of zinc oxide can be obtained during the manufacture of the zinc oxide. Where micronizing techniques are employed, the zinc oxide may be micronized to the desired particle size range by conventional techniques, for example, using a ball mill, ultrasonic means, or preferably using fluid energy attrition mills such as the trost fluid energy mill from Plastomer Products, Newton, Pa. 18940. When using a fluid energy attrition mill, the desired particle size can be obtained by varying the feed rate of the zinc oxide into the mill. Preferably, the micronized zinc oxide is of sufficient quality to meet or comply with appropriate government regulations.

The propellant is the gas in the aerosol canister or pressure bottle for expelling the contents when the pressure is released. The gas or gases should have a sufficiently high vapor pressure in the aerosol canister to pressurize the contents of the canister to expel the composition from the aerosol canister. Suitable propellants include ethers such as dimethyl ether (DME); and aliphatic hydrocarbons such as the $C_3$ to $C_5$ hydrocarbons, including propane, butane, n-butane, isobutane or mixtures thereof. Such propellants, individually, have vapor pressures ranging from about 17 to about 100 psig at 70° F., preferably from about 25 to about 50 psig at 70° F. The amount of propellant in the aerosol can range from about 10 to about 90% (wt), preferably from about 40 to about 85%, more preferably from about 65 to about 80%, most preferably about 70 to about 77%.

The solvent can be any substance capable of carrying and/or maintaining the micronized zinc oxide and other ingredients in the composition in a substantially uniform mixture or suspension for uniform expulsion and dissipation from from the aerosol canister to the target foot and/or shoe. Suitable solvent can include water; and organic solvents capable of evaporating from the skin or shoe surface such as $C_1$ to $C_3$ alcohols, including methanol, ethanol, propanol and isopropanol. The solvent is used in amounts effective to carry and/or maintain the micronized zinc oxide and other ingredients in the composition in a substantially uniform mixture or suspension in the presence of a pressurizing propellant. The amount of solvent in the composition of the aerosol can from about zero to about 80 percent, preferably from about 4 to about 50 percent, more preferably from about 5 to about 20 percent. Without the propellant, the amount of solvent in the composition or concentrate can range from about zero (0) to about 80% by weight, more preferably from about 20 to about 75%.

Optionally, a fragrance (an aromatic compound) can be added to the composition or aerosol to impart an aesthetically pleasing aroma to the composition or aerosol and to mask any foot and shoe odors. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. The fragrance may also be encapsulated. One or more fragrances can optionally be included in the aerosol in an amount ranging from about 0 to about 5 percent, preferably from about 0.01 to about 5 weight percent, also preferably about 0.1 to about 3 percent, more preferably from about 0.2 to about 2.5 percent. Without the propellant, the amount of fragrance in the composition or concentrate can range from about zero to about 15% by weight, preferably from about one to about 11%.

Optionally, a thickening agent can also be added to the composition or aerosol to thicken the contents of the aerosol, including the micronized zinc oxide, the solvent solvent and any other ingredients, to maintain more uniformly or homogenously the ingredients in the aerosol. Suitable thickening agents include Bentone® thickener which is an organically modified hectorite (marketed by Rheox Inc. of Hightstown, N.J.), fatty alcohols such as cetyl, lauryl, stearyl, and the like; soaps such as sodium stearate, sodium myristate and the like, bentonite, cellulosic ethers such as methyl cellulose, sodium cellulose glycollate (sodium carboxymethyl cellullose), silica gel, alumina gel or mixtures thereof. A thickening agent may optionally be included in the composition of the aerosol in an amount ranging from about 0 to about 1 percent, preferably from about 0.1 to about 1 percent, more preferably from about 0.2 to about 1 percent. Without the propellant, the amount of thickening agent in the concentrate can range from about 0.1 to about 5% by weight, more preferably from about 0.2 to about 3%.

Optionally, a base may be added to neutralize any organic or inorganic acids present on the foot or shoe interior. Suitable bases include alkaline earth oxides such as calcium oxide and magnesium oxide; carbonates such as sodium carbonate and sodium bicarbonate; and organic bases such as triethanolamine and aminoethylpropanol (AMP). The base may optionally be included in the composition of the aerosol in an amount ranging from about 0 to about 10 percent, preferably from about one to about 5 percent. Without the propellant, the amount of base in the composition or concentrate can range from about zero to about 30% by weight, more preferably from about 5 to about 25%.

The aerosol container or can may be made of any suitable material capable of being pressurized with the propellant. Such materials can include rolled steel, aluminum, tin and mixtures or alloys thereof.

The following examples describe embodiments of the present invention which may be practised, but they are not to be interpreted as limiting the scope of the claims.

EXAMPLE 1

Foot Deodorant Aerosol

| Ingredient | % wt/wt basis in aerosol (with propellant) | % wt/wt basis in concentrate (no propellant) |
|---|---|---|
| Isobutane Propellant | 77.00 | 0.00 |
| Micronized Zinc Oxide | 4.25 | 18.5 |
| Ethyl Alcohol | 17.22 | 75.0 |
| Sodium Bicarbonate | 1.28 | 5.5 |
| Fragrance | 0.25 | 1.0 |
| TOTAL | 100.0 | 100.0 |

To an explosion proof jacketed batch tank, mix about two-thirds of the ethyl alcohol and the sodium bicarbonate. Pass the mixture through a colloid mill. Mix in the remaining ethyl alcohol, the micronized zinc oxide and the fragrance to form a concentrate. Pass the concentrate through a colloid mill and fill an aerosol can with 23% concentrate and 77% isobutane propellant.

EXAMPLE 2

Foot Deodorant Aerosol

| Ingredient | % wt/wt basis in aerosol (with propellant) | % wt/wt basis in concentrate (no propellant) |
|---|---|---|
| Isobutane Propellant | 77.0 | 0.0 |
| Micronized Zinc Oxide | 10.0 | 43.5 |
| Ethyl Alcohol | 6.0 | 26.0 |
| Sodium Bicarbonate | 4.0 | 17.5 |
| Bentone | 0.5 | 2.1 |
| Fragrance | 2.5 | 10.9 |
| TOTAL | 100.0 | 100.0 |

Essentially the same procedure as in Example 1 is employed, except that Bentone is added to the concentrate and the percentages of the remaining ingredients are modified.

EXAMPLE 3

Testing the Aerosol

Protocol

A study was conducted to evaluate the effectiveness of the aerosol foot deodorant of Example 1 in reducing foot odor of at least moderate severity. Subjects were selected with particularly intense foot odor. Subjects discontinued the use of all foot products at least 48 hours prior to enrollment. They chose a pair of shoes (or sneakers) to wear for at least 8 hours each day and wore the same type of socks/hosiery throughout the study. Odor was scored in accordance with an 11-point malodor intensity scale ranging from zero to 10. In this scale, an average malodor score of zero is none or no odor, 5 is moderate odor, 7 is moderately strong odor, 8 is strong odor and 10 is extremely strong odor. Subjects applied aerosol spray cans containing the propellant formulation of Example 1 once each day, in the morning before dressing, to the foot and the corresponding shoe. When applied to the foot, the aerosol was applied to the sole and between the toes. When applied to the shoe, the aerosol was applied to the entire inside area of the shoe that goes on the foot. Foot, shoe and sock odors were evaluated on the first (baseline), third and eight day.

Results. Significant reductions in average overall (moderate and severe) odor scores were achieved for shoe odor by the third day and for foot, shoe, sock and combined odor scores by the eighth day. Also, the aerosol was also able to significantly eliminate foot wetness. The aerosol significantly prevent foot odor before it started when applied to clean feet. The aerosol also significantly prevented foot wetness before it started when applied to dry feet. The aerosol also significantly kept foot wetness under control throughout the day. The results show that an aerosol containing micronized zinc oxide was highly effective in controlling moderate to severe foot odors.

The invention claimed is:

1. A pressurized aerosol composition for treating foot and shoe disorders, consisting essentially of
   a) micronized zinc oxide;
   b) a propellant for expelling contents of an aerosol container when pressure is released, wherein said propellant is present in an amount of about 40% to about 85%;
   c) about 4 to about 50 percent of a solvent selected from the group consisting of water and $C_1$ to $C_3$ alcohols, wherein said pressurized aerosol composition is for treating foot and shoe disorders.

2. The composition according to claim 1 further comprising a fragrance to help mask any foot odors and/or provide a more pleasant odor to the foot or shoe.

3. The composition according to claim 1 further comprising a thickening agent capable of thickening the contents of the aerosol.

4. The composition according to claim 1 further comprising a base to neutralize any organic or inorganic acids.

5. The composition according to claim 1, wherein the amount of micronized zinc oxide in the aerosol is in the range of from about 0.5% to about 15% by weight.

6. The composition according to claim 5, wherein the amount of micronized zinc oxide in the aerosol is in the range of from about 2% to about 12% by weight.

7. The composition according to claim 6, wherein the amount of micronized zinc oxide in the aerosol is in the range of from about 3% to about 10% by weight.

8. The composition according to claim 1, wherein the average particle size of the zinc oxide is in the range from about 26 to about 46 nanometers.

9. The composition according to claim 2, wherein the average particle size of the zinc oxide is in the range from about 30 to about 40 nanometers.

10. The composition according to claim 9, wherein the average particle size of the zinc oxide is in the range from about 35 to about 37 nanometers.

11. A method of inhibiting foot or shoe odor comprising administering to a foot or shoe the Composition of claim 1.

* * * * *